United States Patent
Naglreiter

(10) Patent No.: US 6,514,264 B1
(45) Date of Patent: Feb. 4, 2003

(54) EMBOLIC COIL HYDRAULIC DEPLOYMENT SYSTEM WITH PURGE MECHANISM

(75) Inventor: Brett E. Naglreiter, Hollywood, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 365 days.

(21) Appl. No.: 09/585,193

(22) Filed: Jun. 1, 2000

(51) Int. Cl.[7] ............................................. A61M 29/00
(52) U.S. Cl. ....................................... 606/151; 606/108
(58) Field of Search ................................. 606/151, 158, 606/200, 108, 1; 623/1.11; 128/831, 843

(56) References Cited

U.S. PATENT DOCUMENTS

| 4,811,737 | A |  | 3/1989 | Rydell |
|---|---|---|---|---|
| 5,108,407 | A |  | 4/1992 | Geremia et al. |
| 5,122,136 | A |  | 6/1992 | Guglielmi et al. |
| 5,263,964 | A |  | 11/1993 | Purdy |
| 5,334,210 | A |  | 8/1994 | Gianturco |
| 5,350,397 | A |  | 9/1994 | Palermo et al. |
| 5,382,259 | A |  | 1/1995 | Phelps et al. |
| 5,728,065 | A |  | 3/1998 | Follmer et al. |
| 6,238,415 | B1 | * | 5/2001 | Sepetka et al. ............. 606/213 |
| 6,375,669 | B1 | * | 4/2002 | Rosenbluth et al. ........ 606/200 |
| 6,379,374 | B1 | * | 4/2002 | Hieshima .................... 606/200 |

* cited by examiner

Primary Examiner—Michael H. Thaler

(57) ABSTRACT

A medical device for placing a very small embolic coil at a preselected location within a vessel comprising a positioning catheter having a distal tip for retaining a headpiece with an attached embolic coil such that when the catheter is pressurized with a fluid the distal tip of the catheter expands outwardly to release the headpiece and coil at the preselected position. The headpiece has a passageway which extends through the headpiece to permit air to be purged from the catheter prior to insertion of the catheter into the vessel.

12 Claims, 2 Drawing Sheets

EMBOLIC COIL HYDRAULIC DEPLOYMENT SYSTEM WITH PURGE MECHANISM

BACKGROUND OF THE INVENTION

1. Field of the Invention

The present invention relates to a medical device for placing an embolic coil at a preselected location within a vessel of the human body, and more particularly, relates to a catheter having a distal tip for retaining an embolic coil in order to transport the coil to a preselected position within the vessel and a control mechanism for releasing the embolic coil at the preselected position. This device is particularly suited to transport an embolic coil through the tortuous vasculature of the human brain.

2. Description of the Prior Art

For many years flexible catheters have been used to place various devices within the vessels of the human body. Such devices include dilatation balloons, radiopaque fluids, liquid medications and various types of occlusion devices such as balloons and embolic coils. Examples of such catheter devices are disclosed in U.S. Pat. No. 5,108,407, entitled "Method And Apparatus For Placement Of An Embolic Coil"; U.S. Pat. No. 5,122,136, entitled, "Endovascular Electrolytically Detachable Guidewire Tip For The Electroformation of Thrombus In Arteries, Veins, Aneurysms, Vascular Malformations And Arteriovenous Fistulas." These patents disclose devices for delivering embolic coils to preselected positions within vessels of the human body in order to treat aneurysms, or alternatively, to occlude blood vessels at a particular location.

Coils which are placed in vessels may take the form of helically wound coils, or alternatively, may be random wound coils, coils wound within coils or many other such coil configurations. Examples of various coil configurations are disclosed in U.S. Pat. No. 5,334,210, entitled, "Vascular Occlusion Assembly; U.S. Pat. No. 5,382,259, entitled, "Vasoocclusion Coil With Attached Tubular Woven or Braided Fibrous Covering." Embolic coils are generally formed of a radiopaque metallic materials, such as platinum, gold, tungsten or alloys of these metals. Often times several coils are placed at a given location in order to occlude the flow of blood through the vessel by promoting thrombus formation at the particular location.

In the past, embolic coils have been placed within the distal end of the catheter. When the distal end of the catheter is properly positioned the coil may then be pushed out of the end of the catheter with a guidewire in order to release the coil at the desired location. This procedure of placement of the embolic coil is conducted under fluoroscopic visualization such that the movement of the coil through the vasculature of the body may be monitored and the coil may be placed in the desired location. With these placements systems there is very little control over the exact placement of the coil since the coil may be ejected to a position some distance beyond the end of the catheter. As is apparent, with these latter systems, when the coil has been released from the catheter it is difficult, if not impossible, to retrieve the coil or to reposition the coil.

Numerous procedures have been developed to enable more accurate positioning of coils within a vessel. Still another such procedure involves the use of a glue or solder for attaching the embolic coil to a guidewire, which is in turn, placed within a flexible catheter for positioning the coil within the vessel at a preselected position. Once the coil is at the desired position, the coil is held in position by the catheter and the guidewire is pulled from the proximal end of the catheter to thereby cause the coil to become detached from the guidewire and released from the catheter. Such a coil positioning system is disclosed in U.S. Pat. 5,263,964, entitled, "Coaxial Traction Detachment Apparatus And Method."

Another coil positioning system utilizes a catheter having a socket at the distal end of the catheter for retaining a ball which is bonded to the proximal end of the coil. The ball, which is larger in diameter than the outside diameter of the coil, is placed in a socket within the lumen at the distal end of the catheter and the catheter is then moved into a vessel in order to place the coil at a desired position. Once the position is reached, a pusher wire with a piston at the end thereof is pushed distally from the proximal end of the catheter to thereby push the ball out of the socket in order to thereby release the coil at the desired position. Such a system is disclosed in U.S. Pat. No. 5,350,397, entitled, "Axially Detachable Embolic Coil Assembly." One problem with this type of coil placement system which utilizes a pusher wire which extends through the entire length of the catheter and which is sufficiently stiff to push an attachment ball out of engagement with the socket at the distal end of the catheter is that the pusher wire inherently causes the catheter to be too stiff with the result that it is very difficult to guide the catheter through the vasculature of the body.

Another method for placing an embolic coil is that of utilizing a heat releasable adhesive bond for retaining the coil at the distal end of the catheter. One such system uses laser energy which is transmitted through a fiber optic cable in order to apply heat to the adhesive bond in order to release the coil from the end of the catheter. Such a method is disclosed in U.S. Pat. No. 5,108,407, entitled, "Method And Apparatus For Placement Of An Embolic Coil." Such a system also suffers from the problem of having a separate fiber optic element which extends throughout the length of the catheter with resulting stiffness to the catheter.

Still another coil deployment system incorporates a catheter having a lumen throughout the length of the catheter and a distal tip for retaining the coil for positioning the coil at a preselected site. The distal tip of the catheter is formed of a material which exhibits the characteristic that when the lumen of the catheter is pressurized the distal tip radially expands to release the coil at the preselected site. Such a deployment system is disclosed in the parent patent application, U.S. patent application Ser. No. 09/177,848, filed on Oct. 22, 1998, now U.S. Pat. No. 6,113,662 and entitled, "Embolic Coil Hydraulic Deployment System," assigned to the assignee of the present patent application.

A still further coil deployment system comprising a similar catheter having a distal tip which radially expands to release the coil at a preselected location, however in this system the embolic coil is mounted on a headpiece which extends out of the proximal section of the coil and is in turn disposed in the lumen of the distal tip of the catheter. When the headpiece is released, the headpiece and attached coil then become deployed at the preselected site. Such a deployment system is disclosed in co-pending U.S. Patent Application filed on May 30, 2000 and entitled, "Small Diameter Embolic Coil Hydraulic Deployment System," and assigned to the same assignee as the present patent application.

It has been found that prior to introducing the catheter deployment system into the body it may be desirable to purge air from the catheter to prevent air from being introduced into a vessel. Such a procedure has been used to purge air from the balloon catheter prior to inserting the balloon catheter into a vessel. An example of such a device is shown in U.S. Pat. No. 5,728,065 to Follmer, et al. which discloses a balloon catheter with a vent hole disposed near the distal end of the balloon. The vent hole normally lays against the surface of an inner tubular member, preventing gases from entering the balloon. During purging, the balloon is inflated, the distal end of the balloon opens exposing the vent hole, and gases and a portion of the inflation medium flow out. Another example is shown in U.S. Pat. No. 4,811,737 to Rydell which discloses a balloon catheter with a slit in the distal portion of the tubular member. Fluid is injected into the catheter and flows through multiple inflation ports to expand the balloon. The purging fluid forces the air within the balloon through the slit in the tubular member.

U.S. patent application Ser. No. 09/515,944, filed on Feb. 29, 2000 and entitled, "Embolic Coil Hydraulic Deployment System With Purge Mechanism" discloses an embolic coil deployment system having a purge hole extending through the side of the catheter body for purging air from the system.

SUMMARY OF THE INVENTION

The present invention is directed toward a very small diameter vascular occlusive coil deployment system for use in placing an embolic coil at a preselected site within a vessel which includes a small diameter, flexible catheter having a distal tip for retaining the coil so that the coil may be moved to the preselected site within the vessel. The catheter has a lumen which extends therethrough the length of the catheter and also includes a distal end which is formed of a material having a durometer such that when a fluid pressure of about 300 pounds per square inch (psi) is applied to the interior of the catheter, the walls of the distal tip expand outwardly, or radially, to thereby increase the lumen of the distal tip of the catheter. The embolic coil is disposed upon and bonded to a cylindrical headpiece which has a diameter slightly greater than the diameter of the lumen of the catheter. The headpiece extends outwardly from the proximal end of the coil and this portion of the-headpiece is disposed within and retained by the lumen at the distal tip of the catheter. A hydraulic injector, such as a syringe, is coupled to the proximal end of the catheter for applying a fluid pressure to the lumen of the catheter. When the coil is placed at a desired position within a vessel, fluid pressure is applied to the lumen of the catheter by the hydraulic injector to thereby cause the walls of the distal tip to expand outwardly, or radially, to release the headpiece which carries with it the coil. The cylindrical headpiece includes a small passageway which extends throughout the length of the headpiece to allow the physician to purge any remaining air from the system prior to inserting the coil deployment catheter into a vessel.

In accordance with another aspect of the present invention, the passageway takes the form of a cylindrical aperture which extends coaxially through the length of the cylindrical headpiece.

In accordance with still another aspect of the present invention, the passageway is of a diameter sufficient to allow the passage of air but resists the flow of a liquid, such as normal saline solution. For example, the diameter is preferably on the order of about 0.0012 inches.

In accordance with another aspect of the present invention, the flexible catheter is comprised of a proximal section and a relatively short distal section. The proximal section is formed of a material which is sufficiently flexible to be passed through the vasculature of the human body and is of a durometer which essentially resists outward expansion when a fluid pressure on the order of about 300 psi is applied to the interior of the catheter. The distal section of the catheter is formed of a material which is also sufficiently flexible to be passed through the vasculature of the body, yet is of a durometer which is significantly lower than the durometer of the proximal section and exhibits the property of expanding outwardly, or radially, when such a fluid pressure is applied to the interior of the catheter to thereby permit the release of the headpiece to thereby release the embolic coil.

In accordance with still another aspect of the present invention, the distal section of the catheter has a durometer in a range of between about 25 D and 55 D.

In still another aspect of the present invention, the embolic coil is comprised of a helical coil having a proximal end, a distal end, and a lumen extending therethrough. A headpiece is partially disposed within the lumen of the proximal end of the coil and the other portion of the headpiece is placed in fluid-tight engagement with the lumen of the catheter.

In another aspect of the present invention, the hydraulic injector for applying a fluid pressure to the interior of the catheter takes the form of a syringe which is coupled to the proximal end of the catheter for, upon movement of the piston, creating a fluid pressure which is applied to the interior of the catheter to thereby cause the release of the embolic coil.

In accordance with another aspect of the present invention, the embolic coil may take the form of other types of implantable devices, such as a vascular filter.

These aspects of the invention and the advantages thereof will be more clearly understood from the following description and drawings of a preferred embodiment of the present invention:

DESCRIPTION OF A PREFERRED EMBODIMENT

Figure 1:
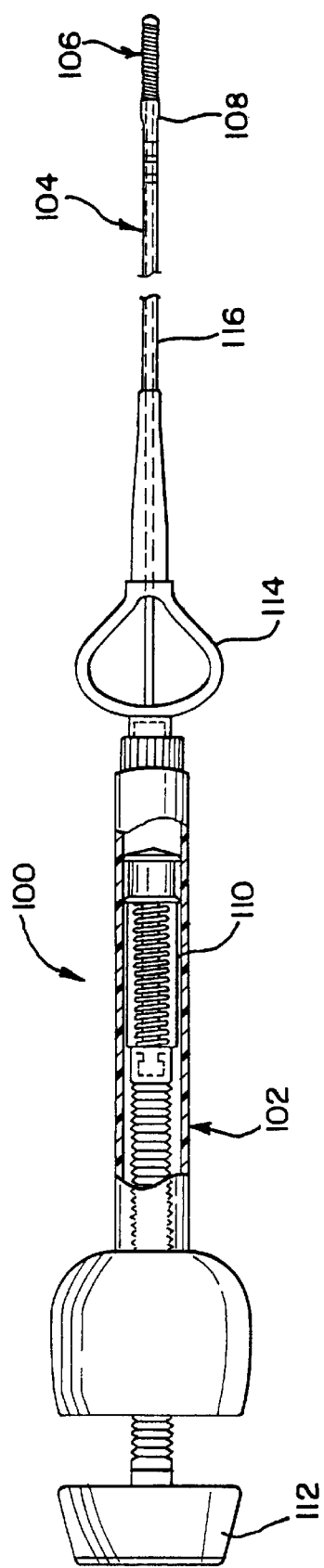
FIG. 1 is an enlarged, partial sectional view of the hydraulic vascular occlusive coil deployment system of the present invention.

FIG. 1 generally illustrates the vascular occlusive coil deployment system 100 which is comprised of a hydraulic injector or syringe 102, coupled to the proximal end of a catheter 104. An embolic coil 106 includes a proximal headpiece 122 which is disposed within the lumen of the distal end 108 of the catheter. The headpiece 122 is tightly held within the lumen of the distal section 108 of the catheter 104 until the deployment system is activated for release of the coil. As may be seen, the syringe 102 includes a threaded piston 110 which is controlled by a handle 112 for infusing fluid into the interior of the catheter 104. Also as illustrated, the catheter 104 includes a winged hub 114 which aides in the insertion of the catheter into the vascular system of the body.

Figure 2:
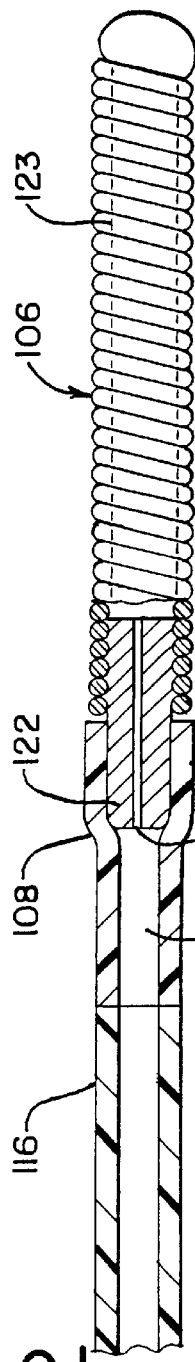
FIG. 2 is an enlarged partially sectional view showing the distal end of the coil deployment system prior to deployment of the coil.

FIG. 2 illustrates in more detail the distal end of the catheter 104. The catheter 104 includes a proximal section 116 and the distal section 108. The embolic coil 106 is tightly wrapped and bonded to the distal portion of a cylindrical headpiece 122. The proximal portion of the headpiece 122 is disposed within the distal section 108 of the catheter and is tightly held within the lumen 120 of this distal section 108 prior to release of the headpiece 122 and attached coil 106. As may be appreciated, FIG. 2 illustrates the vascular occlusive coil deployment system prior to activation of the piston of the syringe and prior to release of the coil.

The embolic coil 106 may take various forms and configurations and may even take the form of a randomly wound coil, however, with the helical wound coil as illustrated in FIG. 2, the coil is provided with a headpiece 122 having a proximal portion which is disposed in a lumen 123 which lumen extends throughout the length of the coil 106. The headpiece 122 serves to retain the coil 106 and also to prevent the flow of fluid through the lumen of the coil 106. When the headpiece 106 is placed in fluid-tight engagement with the lumen 120 the headpiece serves to provide a fluid-tight seal at the distal end of the catheter 104. Adjacent turns of the coil 106 at the proximal end 118 of the coil are preferably continuously soldered or welded together, and are in turn, soldered or welded to the headpiece 122 to provide a generally unitary structure. Most importantly, the diameter of the headpiece is approximately equal to or slightly larger, than the diameter of the lumen of the catheter so that when the headpiece 122 is inserted into the distal section of the catheter, the outside diameter of the attached coil 106 is approximately equal to the outside diameter of the catheter. This construction results in a deployment system having an overall outside diameter approximately equal to that of the catheter.

As illustrated in FIG. 2, the cylindrical headpiece 122 includes a passageway 126 which extends coaxially through the length of the headpiece and is of a diameter which permits the passage of air, but is restrictive to the flow of fluid such as normal saline solution. The passageway is cylindrical and is between about 0.0007 inches and 0.0015 inches in diameter and is preferably about 0.0012 inches.

Prior to inserting the catheter 104 into a vessel of the body, the physician may hold the catheter 104 with the distal end pointing upward to allow any trapped air in the system to move toward the distal end of the catheter and then apply pressure to the syringe to cause the trapped air to pass through passageway 126 and then out of the system. In deploying the embolic coil, the passageway 126 is sufficiently small in diameter to resist the flow of liquid through the passageway so that sufficient pressure is developed to expand the walls of the distal tip of the catheter to release the headpiece 122.

Preferably, the proximal section 116 and the distal section 108 of the catheter 104 are formed of materials having different durometers. The proximal section 116 is preferably formed of Vestimid material having a durometer in a range of about 62 D to 75 D. The proximal section is sufficiently flexible to transverse the vasculature of the human body, but is sufficiently rigid such that when a fluid pressure of approximately 300 psi is applied to the interior of this section of the catheter there is very little, if any, radial expansion of the walls of this section. On the other hand, the distal section 108 of the catheter is preferably formed of polymer material with a relatively low durometer which, exhibits the characteristic that when a fluid pressure of approximately 300 psi is applied to the interior of the catheter the walls of the distal section 108 expand radially, somewhat similar to the action of a balloon inflating, to thereby release the proximal end 118 of the coil 106. As may be appreciated, there are numerous materials which could be used to fabricate the proximal section 116 and distal section 108 of the catheter 104, however, the distal section 108 is preferably formed from a block copolymer such as Pebax having a durometer of between 25 D and 55 D with a durometer of 40 D being the preferred durometer.

Figure 3:
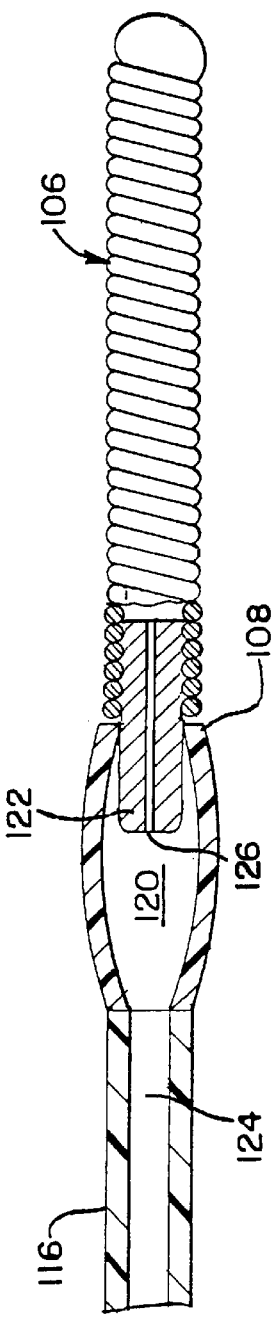
FIGS. 3 and 4 illustrate the sequential steps in the radial expansion of the distal tip of the coil deployment system as the embolic coil is released; and, FIG. 5 illustrates the distal tip of the coil deployment system after release of the embolic coil.
Figure 4:
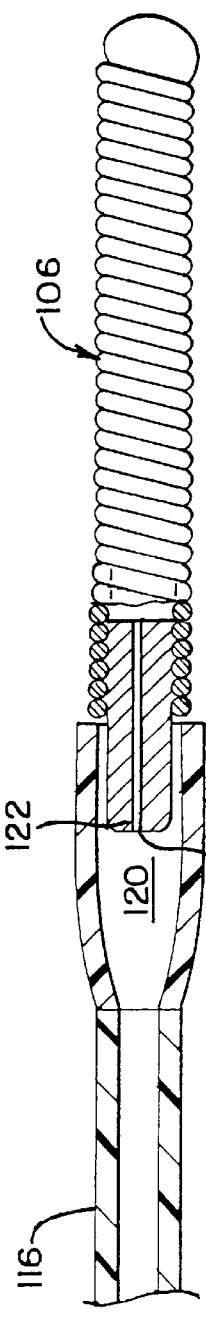

FIGS. 3 and 4 generally illustrate the coil release mechanism in action for the vascular occlusive catheter deployment system. More particularly, as shown in FIG. 3, when a hydraulic pressure is applied to the interior 124 of the catheter 104 the relatively low durometer distal section 108 of the catheter begins to expand radially, much as a balloon expands during the process of inflation. As the distal section 108 continues to expand radially there comes a point as illustrated in FIG. 4 in which the headpiece 122 and attached coil 106 becomes disengaged from the lumen of the distal section 108 and the coil is then released from the catheter and is deployed within the vessel.

Figure 5:
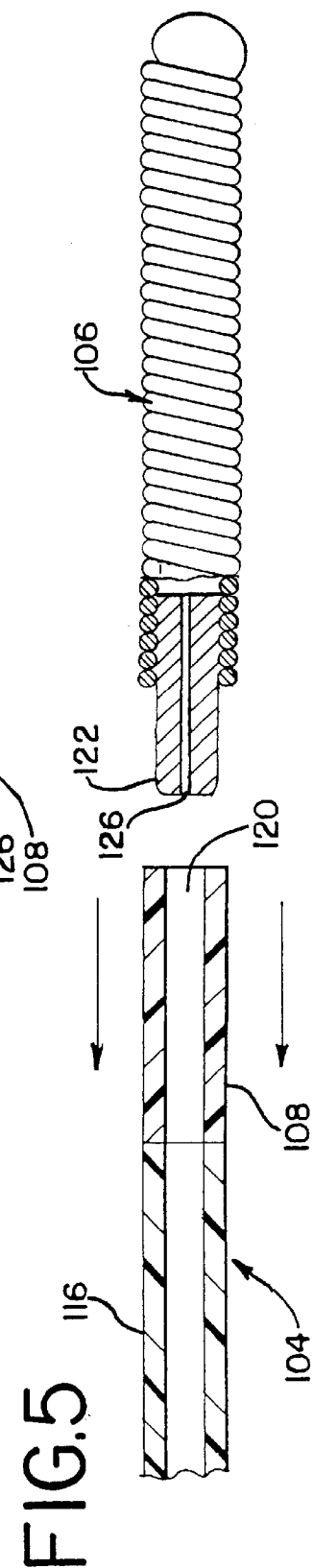

As illustrated in FIG. 5, when the headpiece 122 and the coil 106 have been released from the catheter 104, the catheter may then be withdrawn leaving the coil positioned at the desired site.

With the vascular occlusive coil deployment system of the present invention it is possible to place an embolic coil very precisely at a desired location within a vessel. Once the coil has been placed in that location by use of the catheter, the catheter may be activated by applying a hydraulic pressure to the interior of the catheter to thereby cause the catheter to release the coil and deposit the coil very accurately at the desired location.

As is apparent, there are numerous modifications of the preferred embodiment described above which will be readily apparent to one skilled in the art, such as many variations and modifications of the coil including numerous coil winding configurations, or alternatively other types of implant devices, such as a vascular filter. Also, there are obviously variations of the syringe arrangement for applying a fluid pressure to the interior of the catheter, including many other fluid pressure generating systems for increasing the pressure within the interior of a catheter in order to cause the distal section of the catheter to expand. These modifications would be apparent to those having ordinary skill in the art to which this invention relates and are intended to be within the scope of the claims which follow.

That which is claimed is:

1. A vasoocclusive coil deployment system for use in placing a coil at a preselected site within a vessel comprising:

an elongated flexible catheter having a lumen extending therethrough and having a proximal section and a distal section, said distal section of the catheter being formed of a material having a durometer which exhibits the characteristic that when a fluid pressure is applied to the interior of the catheter the walls of the distal section of the catheter is caused to expand outwardly;

an embolic coil assembly comprised of a helically wound flexible coil having proximal and distal ends and a cylindrical headpiece disposed within the proximal section of the coil, said cylindrical headpiece having a passageway through said headpiece and being of a size which permits the passage of air but resists the flow of a liquid, said embolic coil assembly being disposed in fluid-tight engagement with the lumen of the distal section of the catheter; and, a syringe coupled to the proximal section of the catheter for applying a fluid pressure to the interior of the catheter to thereby cause the distal section of the catheter to expand outwardly to thereby release the embolic coil.

2. A vasoocclusive coil deployment system as defined in claim 1, wherein said cylindrical headpiece includes a proximal and a distal section, said coil is tightly wound about the distal section of the headpiece and the proximal section of the headpiece is disposed in fluid-tight engagement with the lumen of the distal section of the catheter.

3. A vasoocclusive coil deployment system as defined in claim 1, wherein said passageway extends coaxially through the cylindrical headpiece.

4. A vasoocclusive coil deployment system as defined in claim 2, wherein said passageway extends coaxially through the cylindrical headpiece.

5. A vasoocclusive coil deployment system as defined in claim 1, wherein said passageway is circular and has a diameter of between approximately 0.0007 inches and 0.0015 inches.

6. A vasoocclusive coil deployment system as defined in claim 1, wherein said passageway is circular and has a diameter of approximately 0.0012 inches.

7. A vasoocclusive coil deployment system for use in placing a coil at a preselected site within a vessel comprising:

an elongated flexible catheter having a lumen extending therethrough and having a proximal section and a distal section, said distal section of the catheter being formed of a material having a durometer which exhibits the characteristic that when a fluid pressure is applied to the interior of the catheter the walls of the distal section of the catheter is caused to expand outwardly;

an embolic coil assembly comprised of a helically wound flexible coil having proximal and distal ends and a cylindrical headpiece disposed within the proximal section of the coil, said cylindrical headpiece having a passageway extending longitudinally through said headpiece and being of a size which permits the passage of air but resists the flow of a liquid, said embolic coil assembly being disposed in fluid-tight engagement with the lumen of the distal section of the catheter; and, a fluid pressure generating device coupled to the proximal section of the catheter for applying a fluid pressure to the interior of the catheter to thereby cause the distal section of the catheter to expand outwardly to thereby release the embolic coil.

8. A vasoocclusive coil deployment system as defined in claim 7, wherein said cylindrical headpiece includes a proximal and a distal section, said coil is tightly wound about the distal section of the headpiece and the proximal section of the headpiece is disposed in fluid-tight engagement with the lumen of the distal section of the catheter.

9. A vasoocclusive coil deployment system as defined in claim 7, wherein said passageway extends coaxially through the cylindrical headpiece.

10. A vasoocclusive coil deployment system as defined in claim 8, wherein said passageway extends coaxially through the cylindrical headpiece.

11. A vasoocclusive coil deployment system as defined in claim 7, wherein said passageway is circular and has a diameter of between approximately 0.0007 inches and 0.0015 inches.

12. A vasoocclusive coil deployment system as defined in claim 11, wherein said passageway is circular and has a diameter of approximately 0.0012 inches.

* * * * *